(12) United States Patent
Waddell

(10) Patent No.: US 10,695,455 B2
(45) Date of Patent: *Jun. 30, 2020

(54) FLEXIBLE ION GENERATOR DEVICE

(71) Applicant: Charles Houston Waddell, Roanoke, VA (US)

(72) Inventor: Charles Houston Waddell, Roanoke, VA (US)

(73) Assignee: Global Plasma Solutions, Inc., Charlotte, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 16/434,678

(22) Filed: Jun. 7, 2019

(65) Prior Publication Data

US 2019/0307914 A1 Oct. 10, 2019

Related U.S. Application Data

(63) Continuation-in-part of application No. 15/816,027, filed on Nov. 17, 2017, now Pat. No. 10,322,205, which is a continuation of application No. 15/412,825, filed on Jan. 23, 2017, now Pat. No. 9,849,208.

(60) Provisional application No. 62/281,318, filed on Jan. 21, 2016.

(51) Int. Cl.
*A61L 9/22* (2006.01)
*H01J 33/02* (2006.01)

(52) U.S. Cl.
CPC ............... *A61L 9/22* (2013.01); *H01J 33/02* (2013.01); *A61L 2209/16* (2013.01)

(58) Field of Classification Search
CPC ......... A61L 9/22; A61L 2209/16; H01J 33/02
See application file for complete search history.

(56) References Cited

U.S. PATENT DOCUMENTS 9,849,208 B2 * 12/2017 Waddell ................ A61L 9/22
10,322,205 B2 * 6/2019 Waddell ................ A61L 9/22
2009/0211459 A1 8/2009 Hu et al.

* cited by examiner

*Primary Examiner* — Nicole M Ippolito
*Assistant Examiner* — Hanway Chang
(74) *Attorney, Agent, or Firm* — Clements Bernard Walker

(57) ABSTRACT

A flexible ion generator device that includes a dielectric layer having a first end, a second end, a first side, a second side, a top side, and a bottom side, at least one trace positioned on the dielectric layer and having a plurality of emitters engaged to the at least one trace, wherein the trace extends along the top side of the dielectric layer and along a substantially parallel plane with respect to either the first side or the second side and in predetermined locations periodically along the length of the dielectric layer, the at least one trace extends downwardly from the parallel plane for a distance and then upwardly towards the parallel plane.

18 Claims, 13 Drawing Sheets

FLEXIBLE ION GENERATOR DEVICE

CROSS REFERENCE TO RELATED PATENT APPLICATION

This application is a continuation-in-part of U.S. patent application Ser. No. 15/816,027, filed Nov. 17, 2017 and entitled "FLEXIBLE ION GENERATION DEVICE", which is a continuation of U.S. Pat. No. 9,849,208 issued Dec. 26, 2017 and entitled "FLEXIBLE ION GENERATION DEVICE", which claims the benefit of U.S. Provisional Patent Application No. 62/281,318, filed on Jan. 21, 2016, and entitled "FLEXIBLE ION ELECTRODE," the contents of which are incorporated in full by reference herein.

FIELD OF THE INVENTION

The present invention relates generally to the field of air treatment, and more particularly to the treatment of air using ionization that is produced using a flexible ion generation device for dispersing the ions into a conduit or a duct.

BACKGROUND OF THE INVENTION

Air and other fluids are commonly treated and delivered for a variety of applications. For example, in heating, ventilation and air-conditioning (HVAC) applications, air may be heated, cooled, humidified, dehumidified, filtered or otherwise treated for delivery into residential, commercial or other spaces.

Needs exist for improved systems and methods of treating and delivering purified air for these and other applications. It is to the provision of improved systems and methods meeting these needs that the present invention is primarily directed.

BRIEF SUMMARY OF THE INVENTION

According to an embodiment of the present invention, the flexible ion generator device includes one dielectric layer, at least one trace having a first end and a second end, the at least one trace is engaged to the dielectric layer, and at least one emitter engaged to the trace for emitting ions.

According to another embodiment of the present invention, the flexible ion generator device incudes an emitter composed of an ion brush containing a plurality of bristles extending therefrom.

According to yet another embodiment of the present invention, the flexible ion generator device includes a trace composed of a conducting material such as copper, brass, stainless steel, titanium, gold, silver, tungsten, carbon, or the like.

According to yet another embodiment of the present invention, the flexible ion generator device includes the at least one trace is positioned in close proximity to the first side of the dielectric layer and generally is parallel with the first side of the dielectric layer, at predetermined distances along the length of the at least one trace, the at least one trace extends downwardly towards the second side of the dielectric layer to a first side of the contact point and then from a second side of the contact point, the at least one trace extends towards the top side of the dielectric layer and extends generally parallel with the top side of the dielectric layer.

According to yet another embodiment of the present invention, the flexible ion generator device includes a coupler having a base that extends to an outer edge and a first pair of opposed sidewalls and a second pair of opposed sidewalls extend upwardly from the outer edge to an upper edge, forming a cavity therein, a top portion is disposed on the upper edge, a slot is formed in one of the sidewalls extending from the external surface to the internal surface for receiving the first end of the dielectric layer.

According to yet another embodiment of the present invention, the flexible ion generator device includes an attachment device disposed on the bottom side of the dielectric layer.

According to yet another embodiment of the present invention, the flexible ion generator device a dielectric layer having a first end, a second end, a first side, a second side, a top side, and a bottom side. At least one trace positioned on the dielectric layer and having a plurality of emitters engaged to the at least one trace, wherein the trace extends along the top side of the dielectric layer along a substantially parallel plane with respect to either the first side or the second side and in predetermined locations periodically along the length of the dielectric layer, the at least one trace extends downwardly from the parallel plane for a distance and then upwardly towards the parallel plane.

According to yet another embodiment of the present invention, the flexible ion generator device wherein the dielectric layer may be cut anywhere along it's length without affecting the operating of the device.

According to yet another embodiment of the present invention, the flexible ion generator device wherein at least one emitter extends upwardly from the dielectric layer.

According to yet another embodiment of the present invention, the flexible ion generator device wherein the emitters face toward either the first side or the second side in an alternating arrangement.

According to yet another embodiment of the present invention, the flexible ion generator device includes a power supply device engaged to the flexible ion generator device.

According to yet another embodiment of the present invention, the flexible ion generator device includes a second trace engaged to the top portion of the second dielectric layer and a third dielectric layer having a top portion and a bottom portion, wherein the bottom portion of the third dielectric layer is engaged to the second trace and the top portion of the second dielectric layer.

According to yet another embodiment of the present invention, the flexible ion generator device includes a dielectric layer having a first end, a second end, a first side, a second side, a top side, and a bottom side. A trace positioned on the dielectric layer and having a plurality of emitters engaged to the trace, wherein the trace extends along the top side of the dielectric layer and along a substantially parallel plane with respect to either the first side or the second side and in predetermined locations periodically along the length of the dielectric layer, the trace extends downwardly from the parallel plane for a distance and then upwardly towards the parallel plane.

According to yet another embodiment of the present invention, the flexible ion generator device includes a plurality of contact points along the trace for receiving the plurality of emitters.

According to yet another embodiment of the present invention, the flexible ion generator devices includes a coupler having a base that extends to an outer edge and a first pair of opposed sidewalls and a second pair of opposed sidewalls extend upwardly from the outer edge to an upper edge, forming a cavity therein, a top portion is disposed on the upper edge, a slot is formed in one of the sidewalls extending from the external surface to the internal surface for receiving the first end of the dielectric layer.

BRIEF DESCRIPTION OF THE DRAWINGS

The present invention is illustrated and described herein with reference to the various drawings, in which like reference numbers denote like method steps and/or system components, respectively, and in which.

DETAILED DESCRIPTION OF THE INVENTION

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
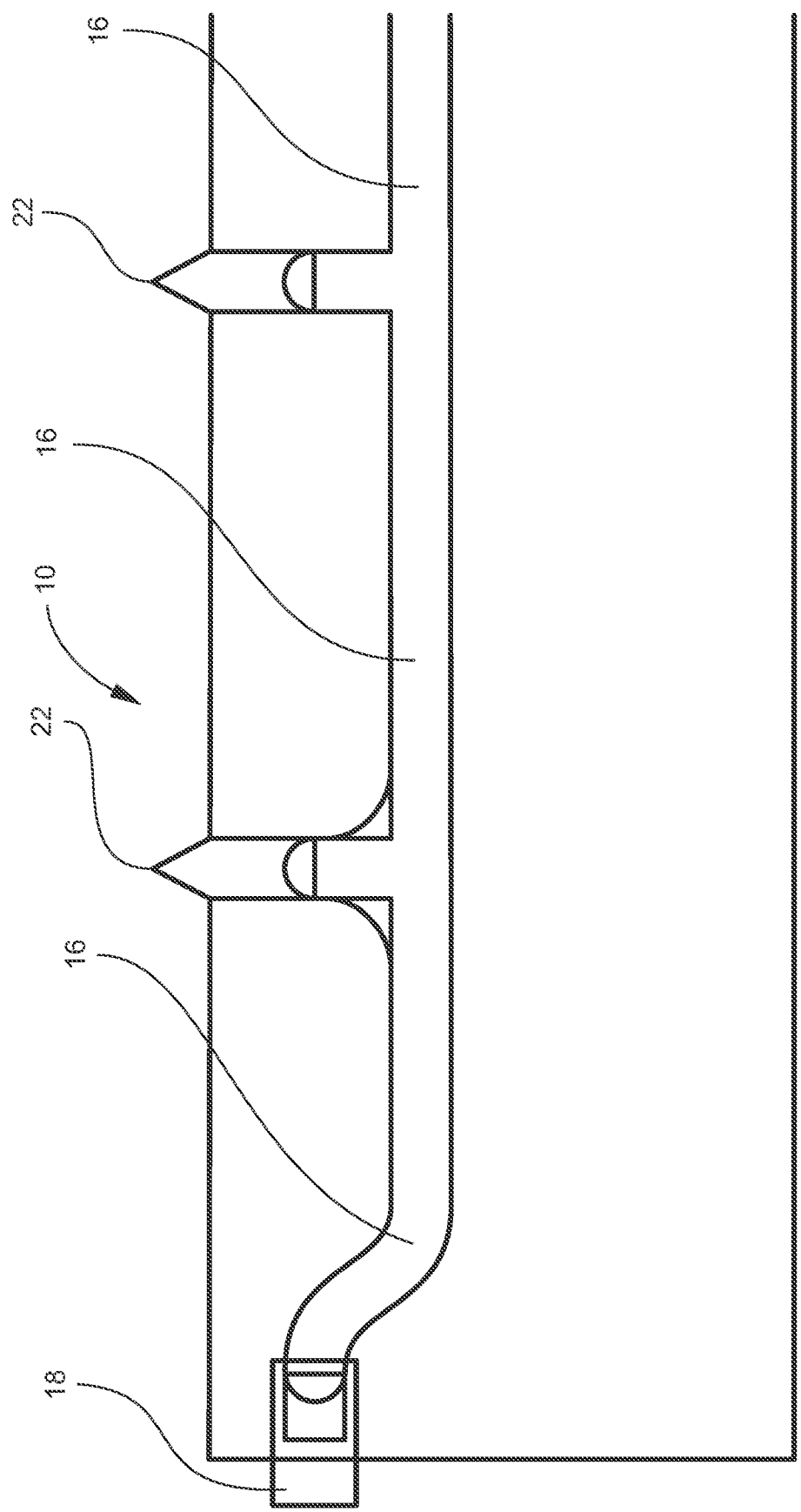
FIG. 1 is a top view of one embodiment of the flexible ion generation device.

Referring now specifically to the drawings, a flexible ion generation device is described herein and illustrated in FIG. 1 and is shown generally at reference numeral 10. The flexible ion generation device 10 has at least a first dielectric layer 12 and, optionally, a second dielectric layer 14. The first dielectric layer 12 contains a top portion, a bottom portion, a top side, a bottom side, a left side, and a right side, wherein the top side and the bottom side are opposed to each other and the left side and the right side are opposed to each other. The second dielectric layer 14 contains a top portion, a bottom portion, a top side, a bottom side, a left side, and a right side, wherein the top side and the bottom side are opposed to each other and the left side and the right side are opposed to each other.

In one embodiment, the flexible ion generation device 10 includes a first dielectric layer 12 having a trace 16 disposed thereon. In another embodiment, the flexible ion generation device 10 includes a first dielectric layer 12 and a second dielectric layer 14 having a trace 16 disposed therebetween (the trace 16 will be considered a first trace when more than one trace is utilized with two or more dielectric layers). The trace 16 has a first end and a second end. The flexible ion generation device 10 may have one or more traces 16, such as copper traces, positioned on the top portion of the first dielectric layer 12. Alternatively, the traces 16 may be composed of other conducting materials such as brass, stainless steel, titanium, gold, silver, tungsten, carbon, mixtures thereof, and the like. The bottom portion of the second dielectric layer 14 is formed over the trace 16 and coupled to the first dielectric layer 12. It will be appreciated that while the trace 16 as illustrated in FIG. 1 is positioned on the top portion of the first dielectric layer 12, the trace 16 may also be positioned on the bottom side of the second dielectric layer 14, and the first dielectric layer 12 is formed over the trace 16 and coupled to the second dielectric layer 14.

As illustrated in FIG. 1, the trace 16 extends longitudinally along the length of the flexible ion generation device 10. In other words, the trace 16 extends from the left side to the right side of the first dielectric layer 12 and the second dielectric layer 14. The trace 16 contains a first end and a second end, whereby the first end is disposed adjacent the right side of the first dielectric layer 12 and second dielectric layer 14 and the second end is disposed adjacent the left side of the first dielectric layer 12 and the second dielectric layer 14. The first end and the second end of the trace 16 may extend beyond the right side and left side of the first dielectric layer 12 and the second dielectric layer 14. A conductive pad or connector 18 may be disposed on the first end and/or the second end of the trace 16. The connector 14 is engaged to a power supply for supplying power to the flexible ion electrode 10, and more specifically the trace 16.

Figure 2:
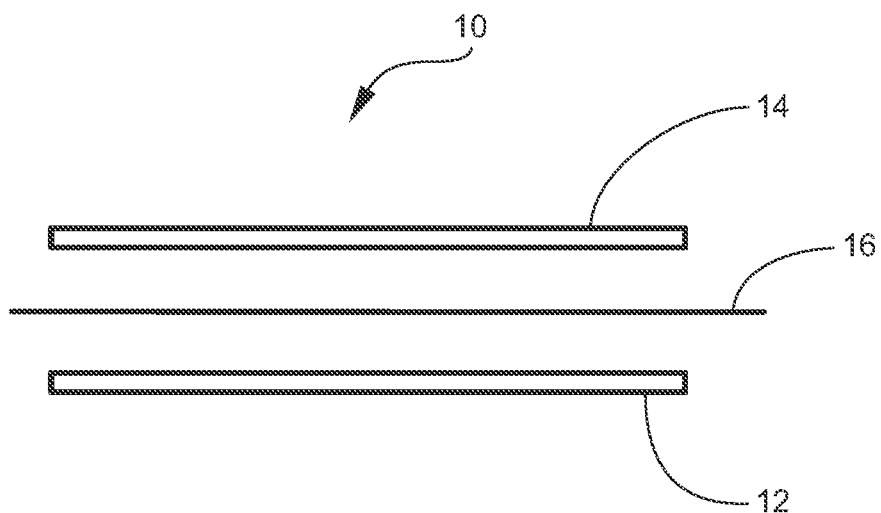
FIG. 2 is an exploded view of one embodiment of the flexible ion generation device.

An emitter 20 may be engaged or etched into the trace 16. As illustrated, the emitter 20 extends to at least the first side and/or second side of the flexible ion electrode 10. As illustrated in FIGS. 1 and 2, the emitter 20 extends to the top side and/or the bottom side of the first dielectric layer 12 and second dielectric layer 14. The emitter 20 extends from the trace 16 to either the top side or bottom side of the the first dielectric layer 12 and the second dielectric layer 14. All emitters 20 of the trace can extend to the same side of the dielectric layer, may alternate sides of the dielectric layer, or may extend to different sides of the dielectric layer at different intervals. The first end of the emitter 20 is etched into the trace 16 and the second end of the emitter 20 extends to a point 22. As illustrated, the emitter 20 at the second end has a gradually reducing width that terminates at a sharp point 22, allowing ions to flow therefrom. The point 22 of the emitter 20 is not connected, coupled, or engaged to the first dielectric layer 12 and second dielectric layer 14 and may extend outwards from these layers (12, 14). In other words, the emitter 20 and/or point 22 may extend beyond the top side or bottom side of the first dielectric layer 12 or and second dielectric layer 14. The point 22 may be coated or plated with a corrosion resistant layer such as gold or other coating material.

Figure 3:
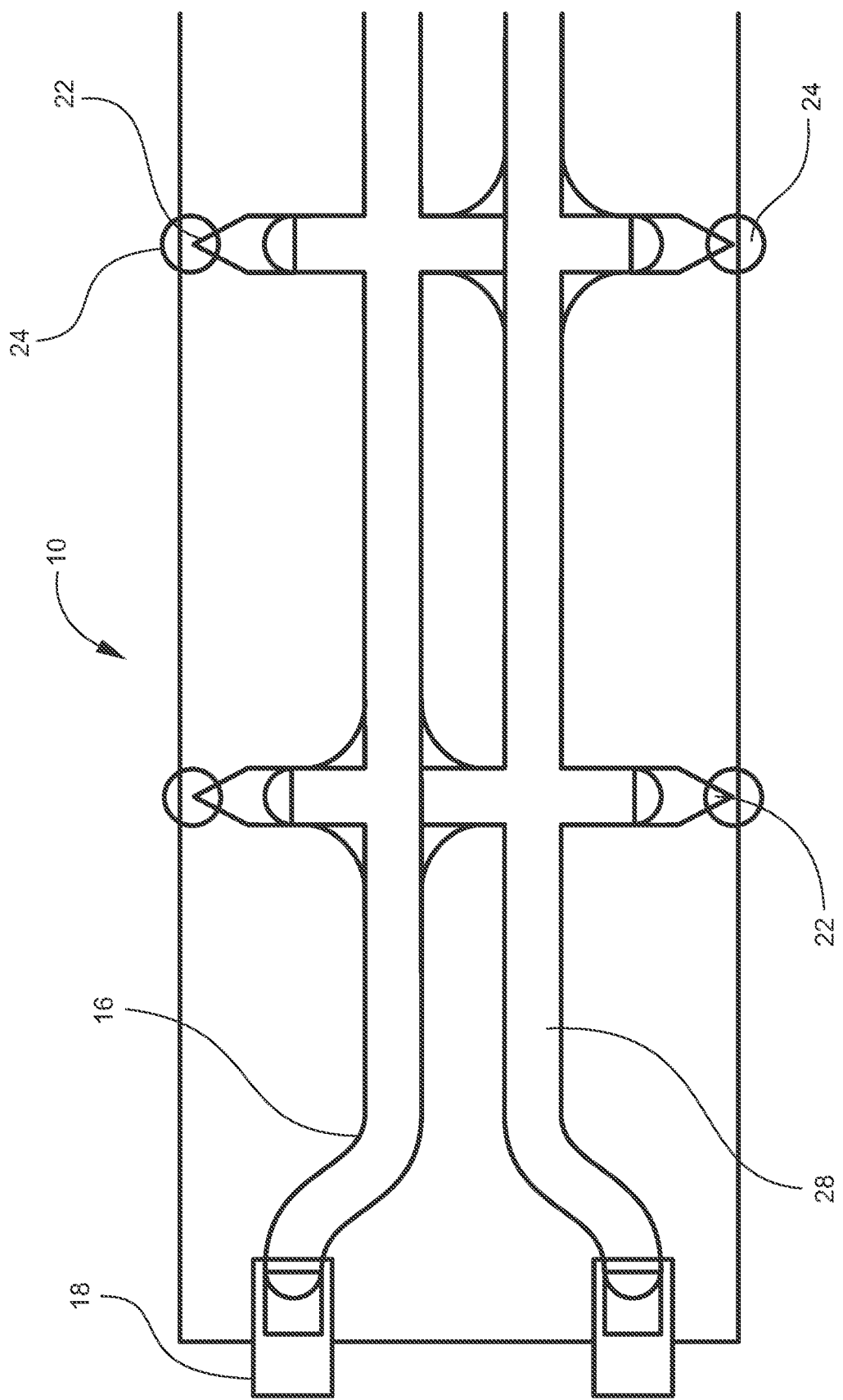
FIG. 3 is a top view of another embodiment of the flexible ion generation device.

The point 22 disposed on the second end of the emitter 20 allows ions to flow therefrom. The trace 16 contains at least one emitter 20, preferably at least two emitters 20, and more preferably a plurality of emitters 20. It is important to note that the first dielectric layer 12 and the second dielectric layer 14 does not cover the point 22, thus allowing ions to flow from the point 22 and into the surrounding area. The dielectric layers (12, 14) adjacent the point may be cut-away, pulled back, or otherwise removed, allowing ions to freely flow from the end of the point 22. In another alternative embodiment, only one dielectric layer may be cut-way, pulled back, or otherwise removed from the point 22 of the emitter. For example and as illustrated in FIGS. 2 and 3, the trace 16 and emitter 20 are disposed on the top portion of the first dielectric layer 12, and the second dielectric layer 14 is formed over the trace 16 and emitter 20 and coupled to the first dielectric layer 12. The point 22 of the emitter 20 does not extend outward from the first dielectric layer 12 and second dielectric layer 14. Instead, the portion of the second dielectric layer that would be cover or be over top the point 22 is cut-away, pulled back, or otherwise removed, forming an opening 24 and allowing ions to emit from the point and into the surrounding area.

In another alternative embodiment, the second dielectric layer 14 may be pre-cut with a portion removed from the top side and/or bottom side in the area where the second dielectric layer 14 will be adjacent or overtop the point 22 forming an opening 24. Therefore, when the second dielectric layer 14 is formed over the trace 16 and emitter 20, the opening 24 is adjacent the point 22, wherein the second dielectric layer 14 does not cover the point 22. In another alternative embodiment, the first dielectric layer 12 and second dielectric layer 14 both are precut with the portion of the respective layer (12, 14) that may be adjacent or overtop the point 22 are removed forming openings 24. Therefore, when the trace 16 and emitter 20 are engaged to the top portion of the first dielectric layer 12, the point 22 is positioned within the opening 24, such that the first dielectric layer 12 will not cover the point 22 and the point 22 is within the opening 24. As the second dielectric layer 14 is formed over the trace 16 and emitter 20, the opening 24 is placed adjacent the point 22, so that the second dielectric layer 14 does not cover the point 22.

An insulating jacket 24 may be positioned over at least a portion of the flexible ion generation device 10. In the cross section shown in FIG. 5, the insulating jacket may encompass the first dielectric layer 12 and second dielectric layer 14 (including trace 16 and a portion of the emitter 20 contained therein). The insulating jacket 24 may surround and protect the dielectric layers (12, 14), including the trace 16 and emitter 20. It should be noted, the insulating jacket 24 does not cover the point 22.

Figure 5:
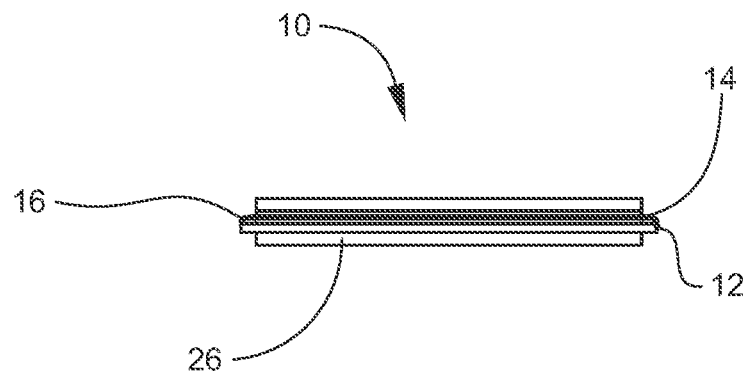
FIG. 5 is a cross-sectional view of another embodiment of the flexible ion generation device.
Figure 6:
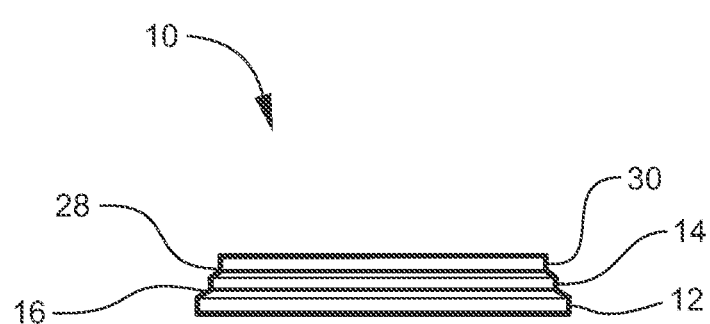
FIG. 6 is a cross-sectional view of another embodiment of the flexible ion generation device.
Figure 7:
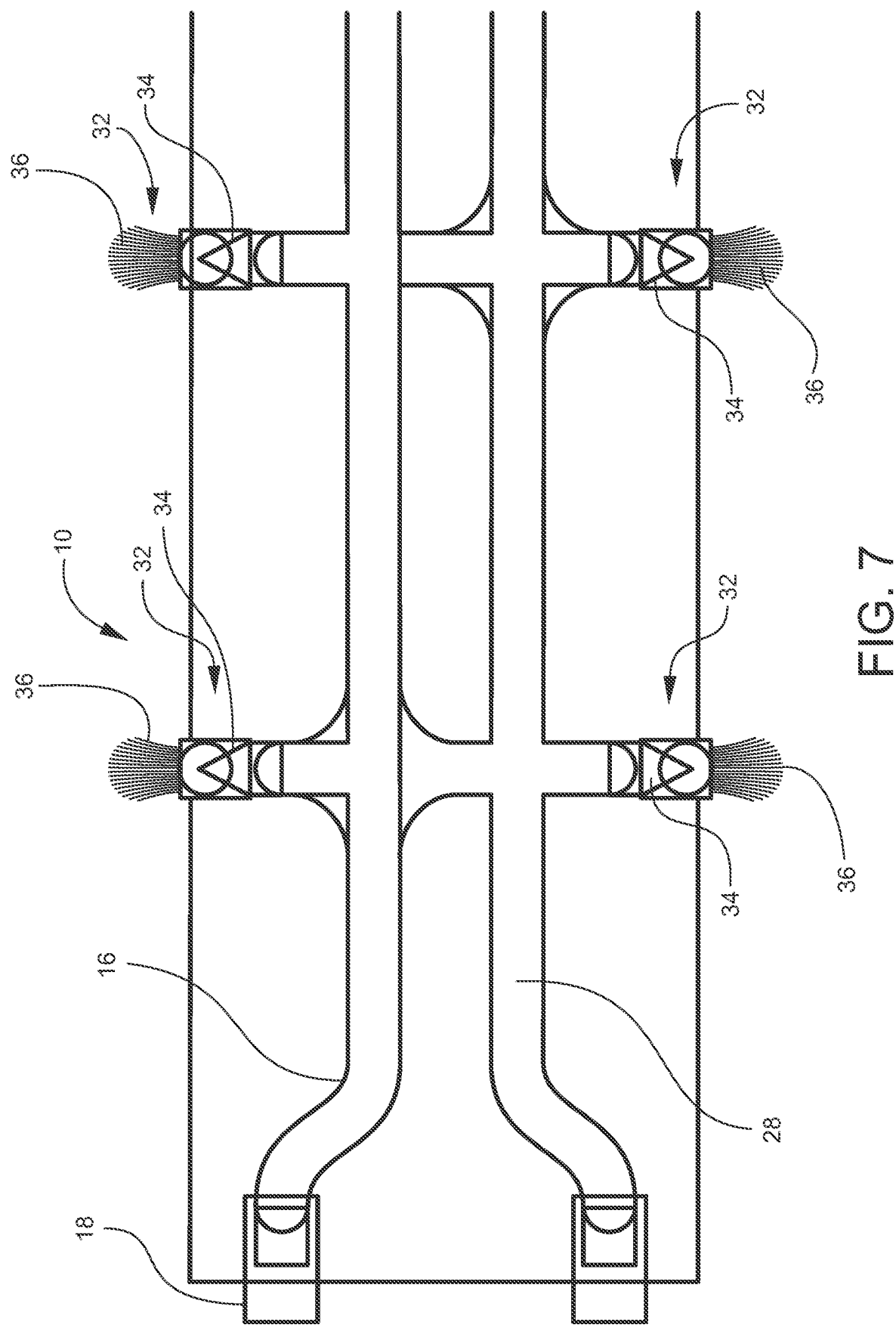
FIG. 7 is a top perspective view of another embodiment of the flexible ion generation device.

In another alternative embodiment and as shown in FIG. 5, the flexible ion generation device 10 may include a second trace 28 and a third dielectric layer 30 (in this embodiment the trace 16 becomes the first trace). The third dielectric layer 30 contains a top portion, a bottom portion, a top side, a bottom side, a left side, and a right side, wherein the top side and the bottom side are opposed to each other and the left side and the right side are opposed to each other.

In this embodiment, the second dielectric layer 14 and third dielectric layer 30 contain the second trace 28 therebetween (and the first trace 16 is disposed between the first dielectric layer 12 and the second dielectric layer 14). The second trace 28 has a first end and a second end. The second trace 28 is positioned on the top portion of the second dielectric layer 14. The bottom portion of the third dielectric layer 30 is formed over the second trace 28 and coupled to the second dielectric layer 14. It will be appreciated that while the second trace 28 may be positioned on the top portion of the second dielectric layer 14, the second trace 28 may also be positioned on the bottom side of the third dielectric layer 30, and the second dielectric layer 14 is formed over the second trace 28 and coupled to the third dielectric layer 30.

Figure 4:
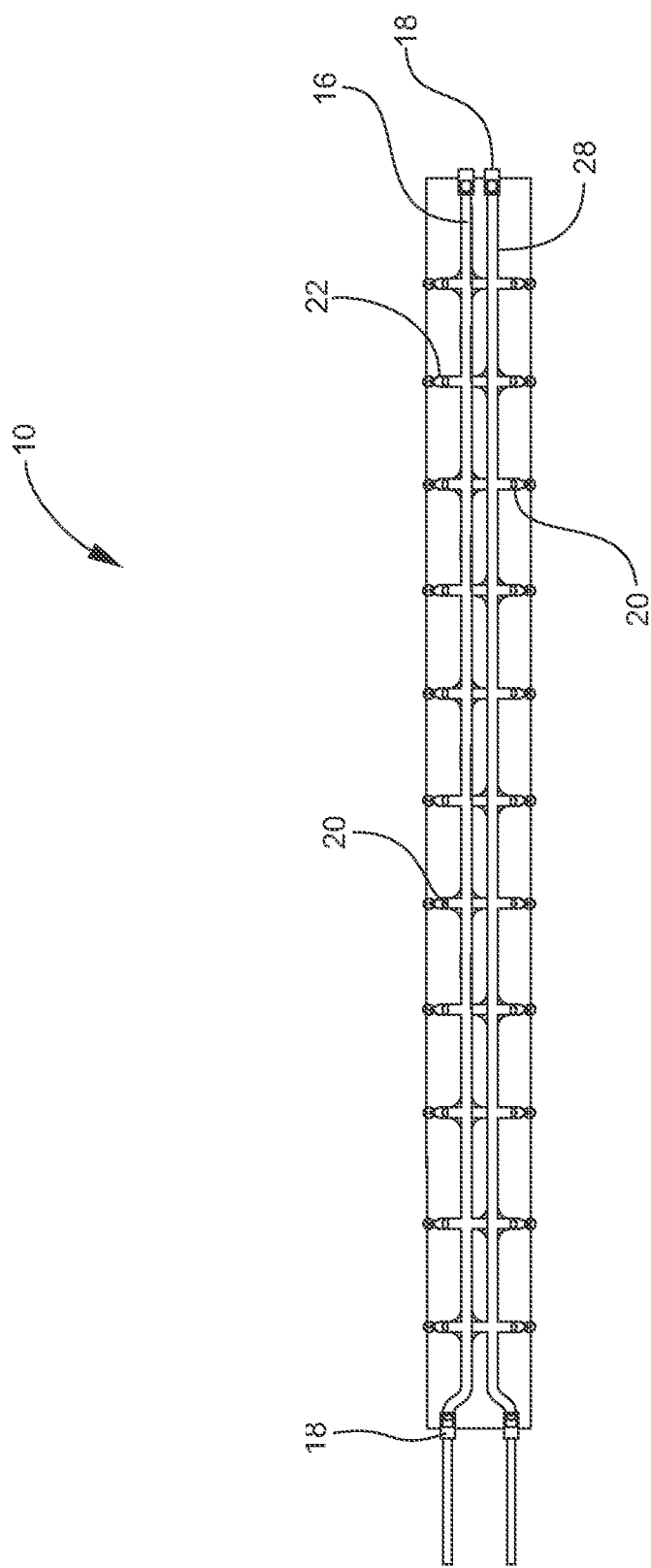
FIG. 4 is a top view of another embodiment of the flexible ion generation device.

As illustrated in FIG. 4, the second trace 28 extends longitudinally along the length of the flexible ion generation device 10. In other words, the second trace 28 extends from the left side to the right side of the second dielectric layer 14 and the third dielectric layer 30. The second trace 28 contains a first end and a second end, whereby the first end is disposed adjacent the right side of the second dielectric layer 14 and third dielectric layer 30 and the second end is disposed adjacent the left side of the second dielectric layer 14 and third dielectric layer 30. The first end and the second end of the second trace 28 may extend beyond the right side and left side of the second dielectric layer 14 and third dielectric layer 30. A conductive pad or connector 18 may be disposed on the first end and/or the second end of the second trace 28. The connector 14 is engaged to a power supply for supplying power to the flexible ion electrode 10, and more specifically, the first trace 16 and second trace 28.

An emitter 20 may be engaged or etched into the second trace 28. As illustrated, the emitter 20 extends to at least the first side and/or second side of the flexible ion electrode 10. As illustrated in FIG. 5, the emitter 20 extends to the top side and/or the bottom side of the flexible ion generation device 10. The emitter 20 extends from the second trace 28 at an angle of about 90° to either the top side or bottom side of the flexible ion generation device 10 and away from the second trace 28. The first end of the emitter 20 is etched into the second trace 28 and the second end of the emitter 20 extends to a point 22. The point 22 of the emitter 20 is not connected, coupled, or engaged to the second dielectric layer 14 and third dielectric layer 30 and extends outwards from these layers (14, 30).

The point 22 disposed on the second end of the emitter 20 allows ions to flow therefrom. The second trace 28 contains at least one emitter 20, preferably at least two emitters 20, and more preferably a plurality of emitters 20. It is important to note that the second dielectric layer 14 and third dielectric layer 30 does not cover the point 22, thus allowing ions to flow from the point 22 and into the surrounding area. The dielectric layers (14, 30) adjacent the point may be cut-away, pulled back, or otherwise removed, allowing ions to freely flow from the end of the point 22. The emitter 20 etched into the second trace 28, extends outward from the second trace 28 and in an opposite direction than the emitter 20 of the first trace 16 extends. In other words, the emitter 20 of the first trace 16 and the emitter 20 of second trace 28 extend in opposite directions and towards opposite sides of the respective dielectric layer (14,30) as illustrated in FIG. 5.

In another alternative embodiment, only one dielectric layer may be cut-way, pulled back, or otherwise removed from the point 22 of the emitter 20. For example and as illustrated in FIG. 5, the second trace 28 and emitter 20 are disposed on the top portion of the second dielectric layer 14, and the third dielectric layer 30 is formed over the second trace 28 and emitter 20 and coupled to the second dielectric layer 14. The point 22 of the emitter 20 does not extend outward from the second dielectric layer 14 and the third dielectric layer 30. Instead, the portion of the third dielectric layer 30 that would cover or be over top the point 22 is cut-away, pulled back, or otherwise removed, forming an opening 24 and allowing ions to emit from the point and into the surrounding area.

In another alternative embodiment, the third dielectric layer 30 may be pre-cut with a portion removed from the top side and/or bottom side in the area where the third dielectric layer 30 will be adjacent or overtop the point 22 forming an opening 24. Therefore, when the third dielectric layer 30 is formed over the trace 16 and emitter 20, the opening 24 is adjacent the point 22, wherein the third dielectric layer 30 does not cover the point 22. The second dielectric layer 14 and the third dielectric layer 30 both are precut with the portion of the respective layer (14, 30) that may be adjacent or overtop the point 22 are removed forming openings 24. Therefore, when the trace 16 and emitter 20 are engaged to the top portion of the second dielectric layer 14, the point 22 is positioned within the opening 24, such that the second dielectric layer 14 will not cover the point 22 and the point 22 is within the opening 24. As the third dielectric layer 30 is formed over the second trace 28 and emitter 20, the opening 24 is placed adjacent the point 22, so that the third dielectric layer 30 does not cover the point 22. Additionally, both sides of the third dielectric layer 30 may have openings on the top side and bottom side, so that the third dielectric layer 30 does not cover the point 22 of the first trace 16.

An insulating jacket 24 may be positioned over at least a portion of the flexible ion generation device 10. The insulating jacket may encompass the first dielectric layer 12, second dielectric layer 14, and third dielectric layer 30 (including the first trace 16, the second trace 28, and a portion of the the emitters 20 contained therein). The insulating jacket 24 may surround and protect the dielectric layers (12, 14, 30), including the trace 16 and emitter 20. It should be noted, the insulating jacket 24 may surround and protect the flexible ion generation device 10, while leaving the points 22 unobstructed for allowing the ions to flow freely and the connectors 18 to facilitate coupling of the flexible ion generation device 10 to a power supply.

In other alternative embodiments of the present invention, any number of dielectric layers may be used with or without a conducting trace in-between each dielectric layer.

An alternative embodiment of the flexible ion generator device 210 is shown in FIGS. 8-14. The flexible ion generator device 210 includes a dielectric layer 212 with a first end, a second end, a first side, a second side, a top side, and a bottom side. A first trace 214, and an optional second trace 216, may be engaged to the top side of the dielectric layer 212 and extend along the top side of the dielectric layer 212 from the first end towards the second end. Periodically spaced along the length of the first trace 214 and the second trace 216 may be a contact point 218. The contact point 218 includes a first face and a second face, wherein the first face is engaged to the top side of the dielectric layer 212. An emitter 220 is engaged to the second face of the contact point 218. Alternatively, the emitter 220 may be disposed on the first trace 214 and/or the second trace 216 or engaged to the first trace 214 or the second trace 216. In another alternative embodiment, the emitters 220 on the first trace 214 may be engaged to a contact point 218 and the emitters 220 on the second trace 216 may be engaged to the second trace 216. Similarly in another alternative embodiment, the emitters 220 on the second trace 216 may be engaged to a contact point 218 and the emitters 220 on the first trace 214 may be engaged to the first trace 214.

The dielectric layer 212 may be a polyamide tape, a silicon tape, or the like that has dielectric properties. One suitable tape sold by DuPont is Kapton®. The dielectric layer 212 is preferably between about 10 mils and 30 mils, and more preferably between about 15 mils to about 25 mils. The dielectric layer 212 is flexible, defined as having flexible characteristics similar to fabric, vinyl, leather, so that the dielectric layer 212 may be bent, rolled-up, twisted, contorted, deformed, misshapen, etc. The first trace 214, and optional second trace 216, may be formed from any substance that can conduct electricity, such as metal, nickel, gold, copper, or copper with nickel/gold plating.

The first trace 214 and the second trace 216 extend along the length of the dielectric layer 212 and substantially parallel to the first side and the second side of the dielectric layer 212. While the first trace 214 is substantially parallel to the first side, periodically, and at a predetermined distance, the first trace 214 extends downwardly to a contact point 218 that is offset from the generally parallel arrangement. In other words, the first trace 214 extends along the length of the dielectric layer 212 for a predetermined distance, and at a predetermined location, the first trace 214 extends slightly towards the second side of the dielectric layer 212. It is important that as the first trace 214 extends towards the second side of the dielectric layer 212 the first trace 214 contains a radius of curvature, meaning there are no points or sharp edges to the first trace 214, but the first trace 214 is rounded as it extends towards the second side of the dielectric layer 212. A contact point 218 may be positioned on the dielectric layer 212 that is offset from the parallel line the majority of the first trace 214 follows. The contact point 218 is generally square and the first trace 214 engages a first corner or first side of the contact point 218. The first trace 214 extends from the opposite side of the contact point 218, and preferably a second corner that is on the opposite side of the contact point 218. The first trace 214 extends towards the first side until it reaches the parallel path and then extends parallel to the first side. Again, the first trace 214 contains a radius of curvature, meaning there are no points or sharp edges to the first trace 214, but the first trace 214 is rounded as it extends towards the first side of the dielectric layer 212.

In other words, the first trace 214 is positioned on the dielectric layer 212 and extends along a substantially parallel plane with respect to the first side or the second side of the dielectric layer 212 and, in predetermined locations periodically along the length of the dielectric layer 212, the first trace 214 extends downwardly from the parallel plane for a distance and then upwardly towards the parallel plane. Likewise, the second trace 216 is positioned on the dielectric layer 212 and extends along a substantially parallel plane with respect to the first side or the second side of the dielectric layer 212 and, in predetermined locations periodically along the length of the dielectric layer 212, the second trace 216 extends downwardly from the parallel plane for a distance and then upwardly towards the parallel plane. A contact point 218 may be placed along the first trace 214 and the second trace 216 for receiving an emitter 220 thereon. Alternatively, the emitters 220 are engaged directly to the first trace 214 and/or the second trace 216

The contact point 218 may be separate and apart the first trace 214. Alternatively, the contact point 218 is integral with the first trace 214 and the first trace 214 forms the contact point 218 and is shaped as a square, rectangle, or other shape for allowing an emitter 220 to be engaged thereto. As illustrated in FIGS. 8-14, a plurality of contact points 218 are disposed along the length of the dielectric layer 212 with each being offset, as described above, from the generally parallel path or plane, with respect to the first side, of the first trace 214.

While the second trace 216 is substantially parallel to the second side, periodically, and at a predetermined distance, the second trace 216 extends downwardly to a contact point 218 that is offset from the generally parallel arrangement. In other words, the second trace 2164 extends along the length of the dielectric layer 212 for a predetermined distance, and at a predetermined location, the second trace 216 extends slightly towards the first side of the dielectric layer 212. It is important that as the second trace 216 extends towards the first side of the dielectric layer 212 the second trace 216 contains a radius of curvature, meaning there are no points or sharp edges to the second trace 216, but the second trace 216 is rounded as it extends towards the first side of the dielectric layer 212. A contact point 218 may be positioned on the dielectric layer 212 that is offset from the parallel line the majority of the second trace 216 follows. The contact point 218 is generally square and the second trace 216 engages a first corner or first side of the contact point 218. The second trace 216 extends from the opposite side of the contact point 218, and preferably a second corner that is on the opposite side of the contact point 218. The second trace 216 extends towards the second side until it reaches the parallel path and then extends parallel to the second side. Again, the second trace 216 contains a radius of curvature, meaning there are no points or sharp edges to the second trace 264, but the second trace 216 is rounded as it extends towards the second side of the dielectric layer 212.

Figure 11:
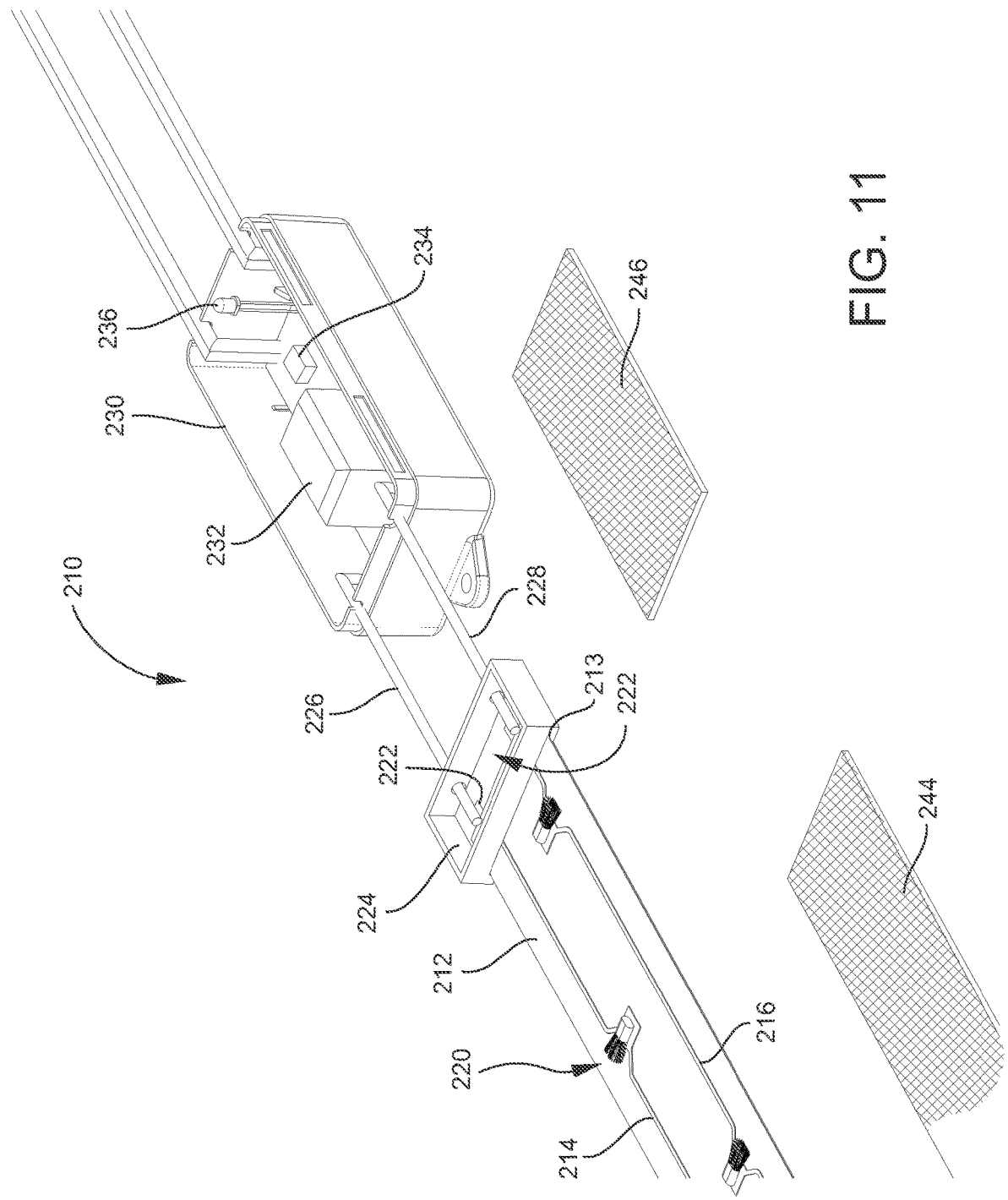
FIG. 11 is a top perspective view of an embodiment of the flexible ion generator device.

A connector 222, similar to the connector 18 shown in FIG. 1, may be disposed on the first end of the first trace 214 and the second trace 216 and disposed on the first end of the dielectric layer 212. As shown in FIG. 11, a coupler 224 is disposed on the first end of the dielectric layer 212. The coupler 224 has a base portion that extends outward to an outer edge, and a first pair and a second pair of opposed sidewalls extend upwardly to an upper edge, forming a cavity therein. The intersection points of the first pair and second pair of opposed sidewalls are defined as corners. A top portion is positioned on the upper edge of the first pair and second pair of opposed sidewalls enclosing the cavity. The first pair of opposed sidewalls are longer than the second pair of opposed sidewalls, as shown in FIG. 11. The front sidewall of the first pair of opposed sidewalls facing the dielectric layer 212 contains a slit 213 therein that extends from the external side to the internal side and into the cavity of the coupler 224. The first end of the dielectric layer 212 is inserted through the slit 213 and retained within the cavity of the coupler 224. As illustrated, the first end of the dielectric layer 212 contains a portion of the first trace 214 and optional second trace 216 along with the connector 222 engaged to the first trace 214 and second trace 216 are disposed within the cavity of the coupler 224. The back sidewall of the first pair of opposed sidewalls facing away from the dielectric layer 212 contains a pair of bores for receiving a first wire 226 and a second wire 228 from the power supply device 230. The first wire 226 contacts the connector 222 engaged to the first trace 214 for supplying power to the first trace 214. The second wire 228 is engaged to the connector 222 engaged to the second trace 216 for supplying power to the second trace 216.

Figure 12:
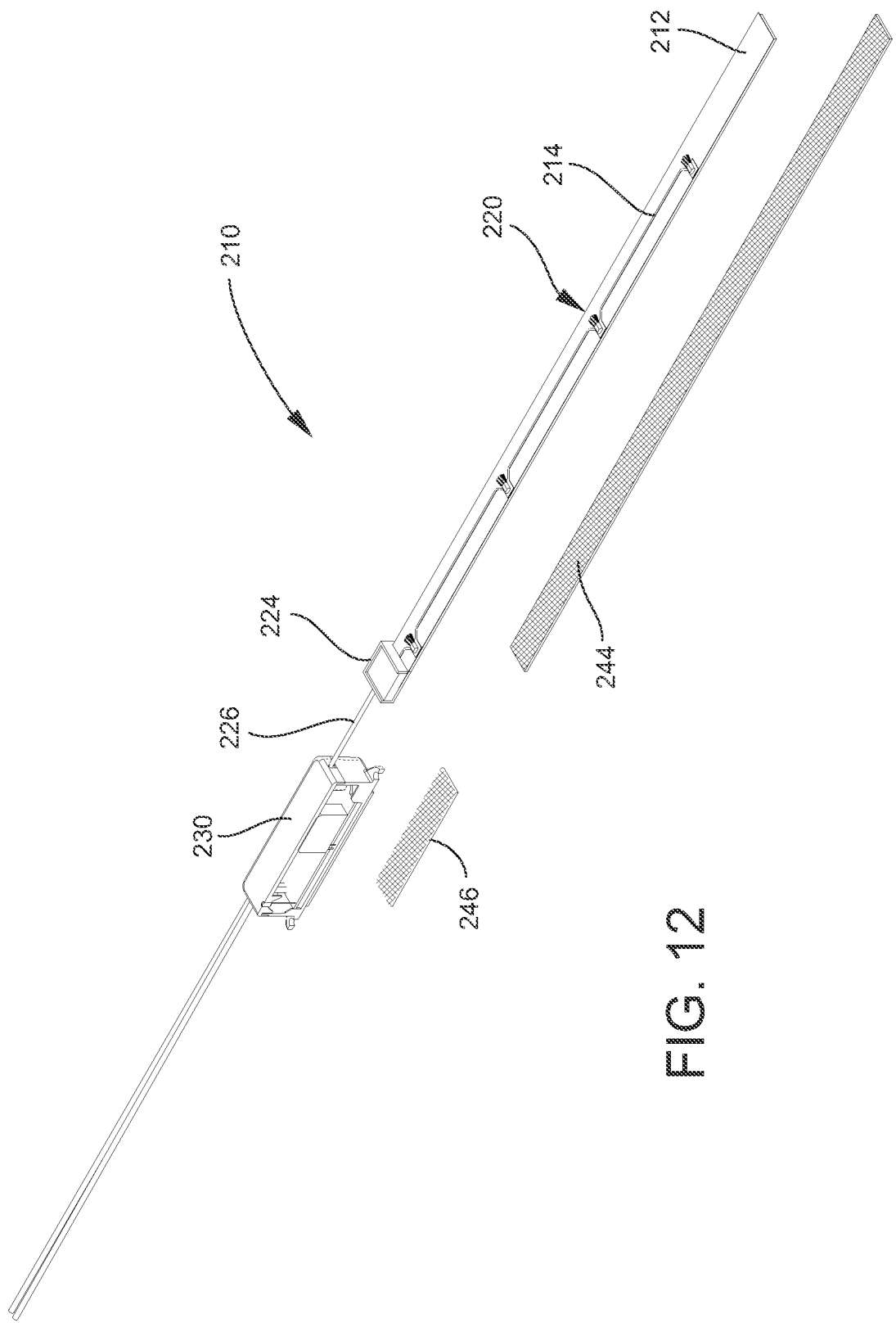
FIG. 12 is a top perspective view of an embodiment of the flexible ion generator device.
Figure 13:
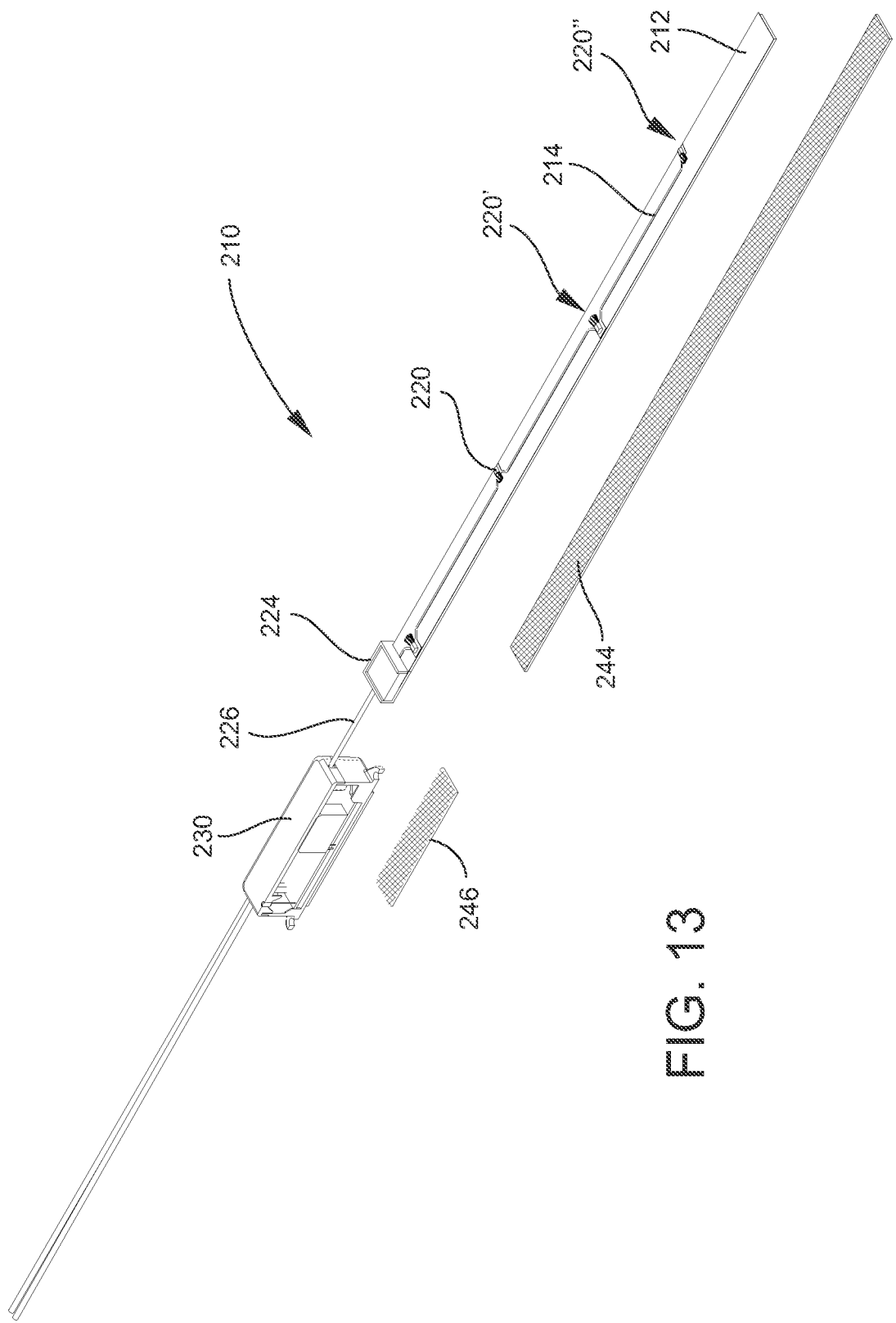
FIG. 13 is a top perspective view of an embodiment of the flexible ion generator device.
Figure 14:
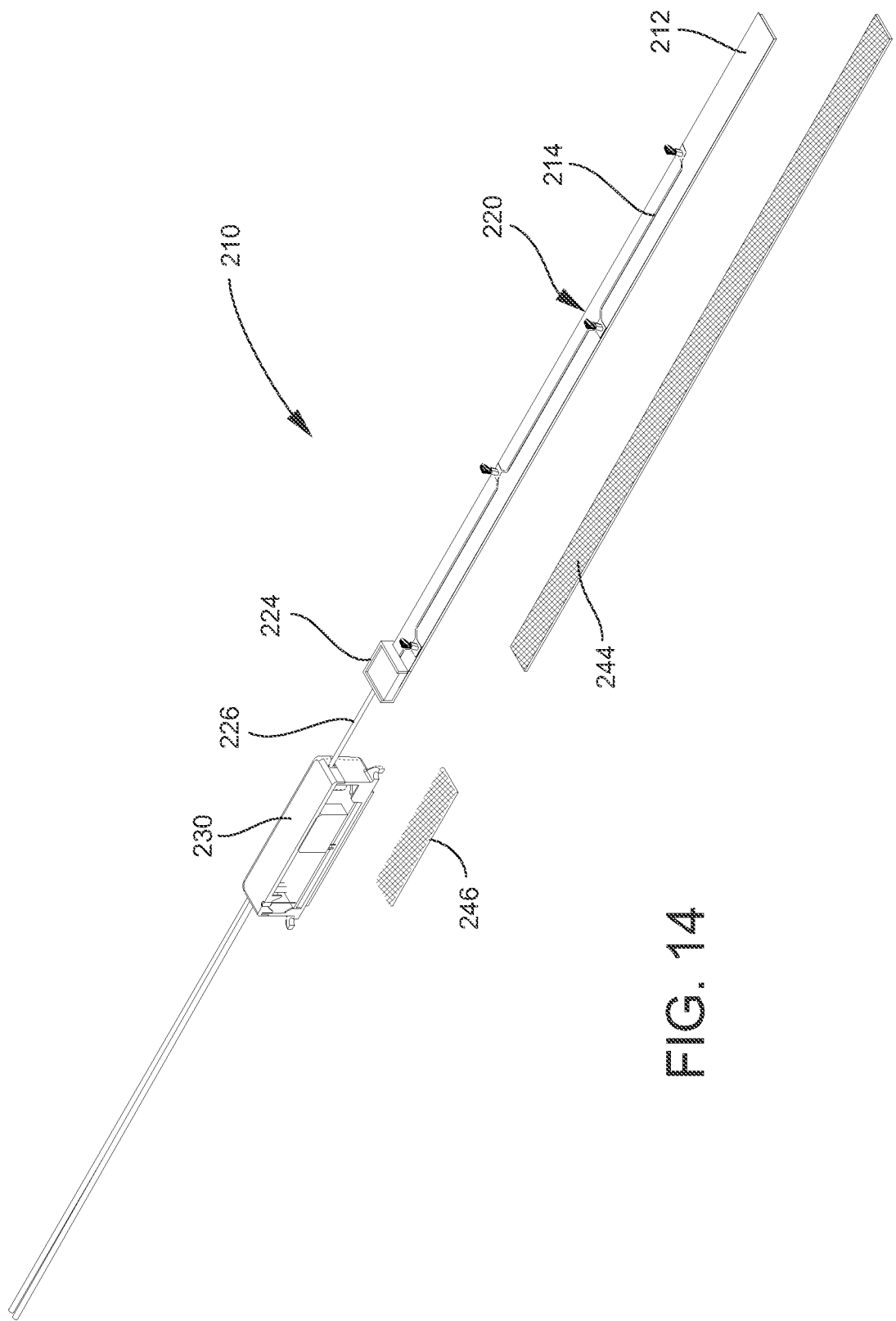
FIG. 14 is a top perspective view of an embodiment of the flexible ion generator device.

In the embodiments illustrated in FIGS. 12-14, there is only one wire 226 extending from the power supply device 230 and into the coupler 224. In this embodiment, the coupler 224 only has one bore for receiving the one wire 226. The wire 226 is engaged to the connector 222 of the first trace 214 in these embodiments for supplying power to the first trace 214.

Figure 8:
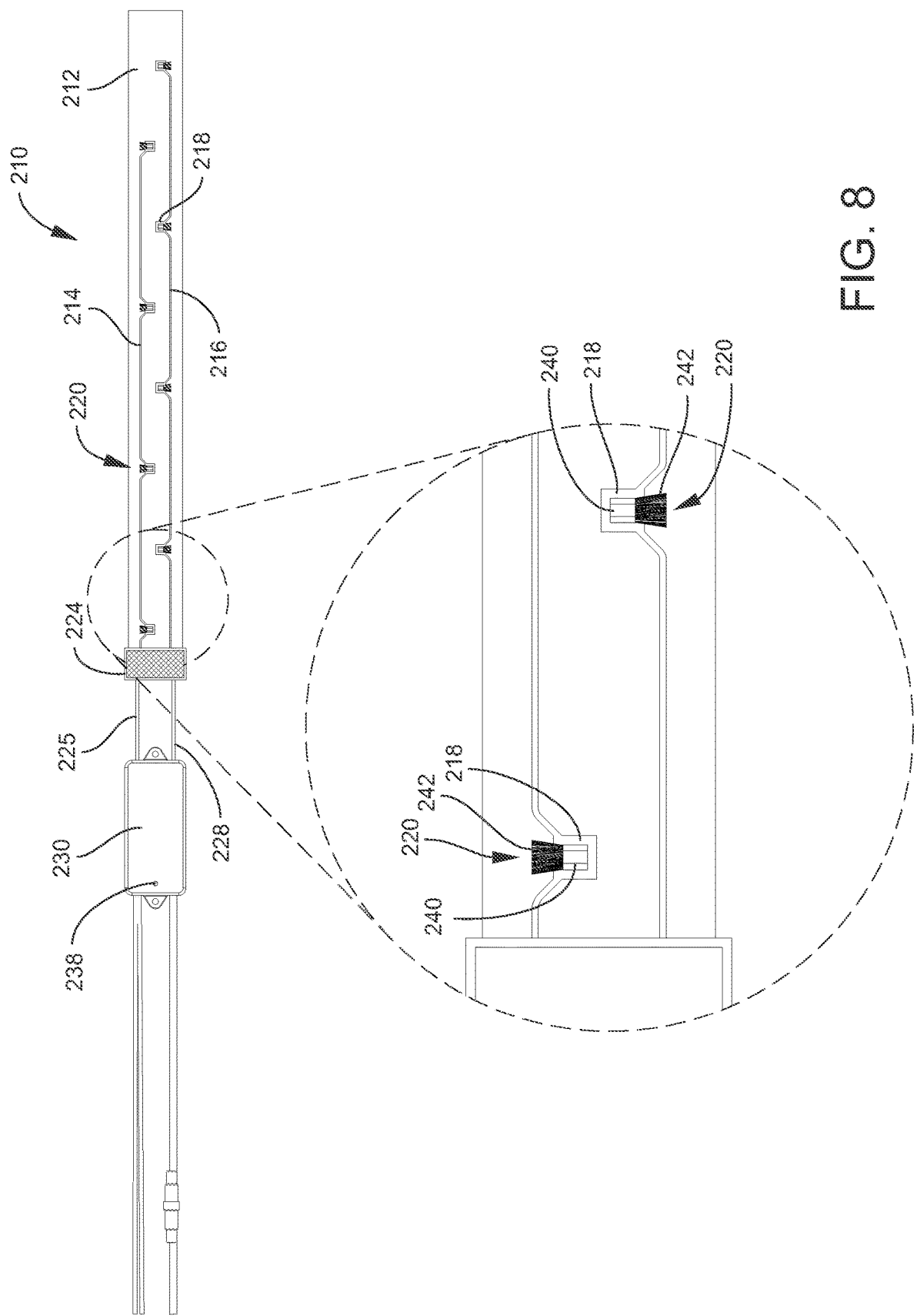
FIG. 8 is a top perspective view of an embodiment of the flexible ion generator device with an enlarged portion.
Figure 9:
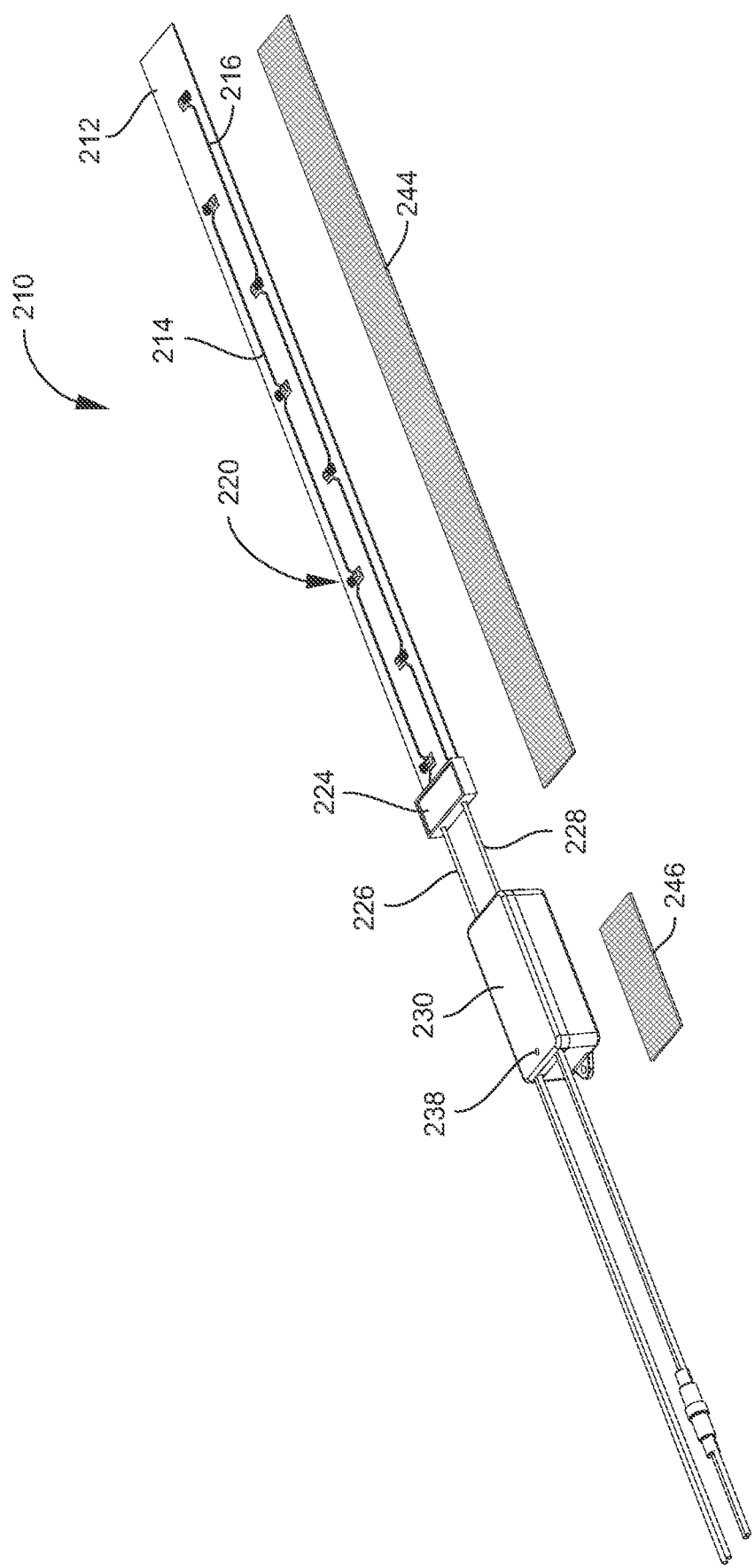
FIG. 9 is a top perspective view of an embodiment of the flexible ion generator device.
Figure 10:
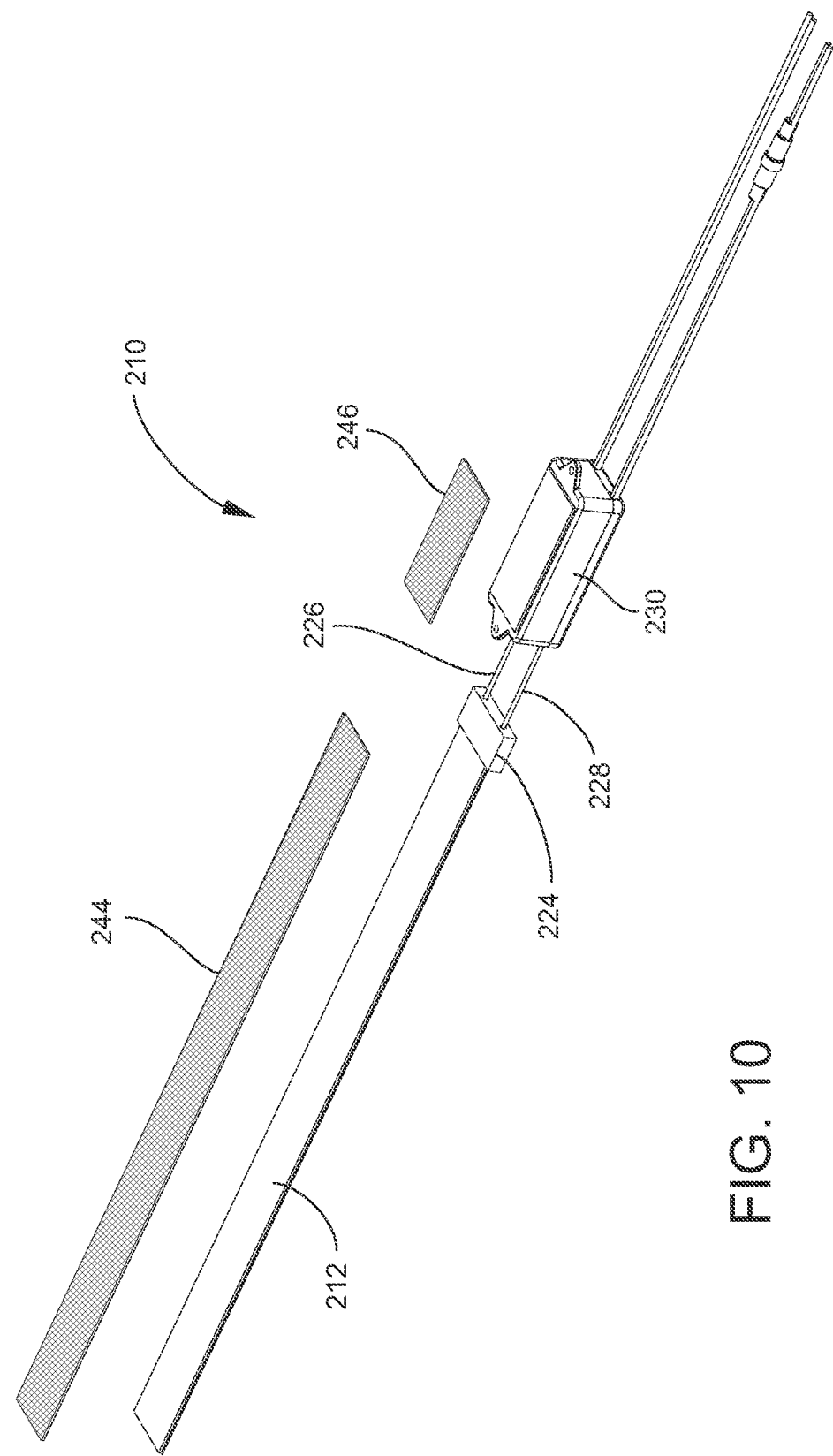
FIG. 10 is a bottom perspective view of an embodiment of the flexible ion generator device.

The power supply device 230 provides alternating current or direct current, with constant or varying frequency, constant or varying voltage and constant or varying current. As illustrated in FIG. 11, the power supply device 230 houses a high voltage transformer 232, a microprocessor 234, and a light emitting-diode (LED) 236. As illustrated, the power supply device 230 is a box, having a base portion that extends outwards to an outer edge and a first pair and a second pair of opposed sidewalls extending upward therefrom to an upper edge, forming a cavity therein. A top portion is engaged to the upper edge and enclosing the cavity. The high voltage transformer 232 and the microprocessor 234 are disposed within the cavity of the power supply device 230. The LED 236 is visible when the top portion is engaged. As illustrated in FIGS. 8 and 9, the top portion contains an opening 238 wherein the LED 236 may extend through the opening 238 or at least be visible through the opening 238. The LED 236 is communicatively coupled to the microprocessor 234, wherein when the device 210 is operating effectively as indicated by the microprocessor, a signal is sent by the microprocessor 234 that illuminates the LED 236. If the device 210 is not operating properly, the microprocessor 234 does not send the signal and the LED 236 is not illuminated. Alternatively, the microprocessor 234 sends a signal to illuminate the LED 236 when the device 210 is not operating properly and no signal is sent when the device 210 is operating properly. Alternatively, the LED 236 may be illuminated by a signal sent by the microprocessor 234 when power is flowing from the power supply device 230 and into the traces (214, 216) and emitting ions.

As shown in FIG. 8, the emitter 220 contains a cap 240 and an ion brush 242, containing a plurality of bristles, extending therefrom. Th cap 240 is preferably composed of metal and surrounds and retains the plurality of the bristles of the ion brush 242. The cap 240 is engaged to the contact point 218, and electricity flows through the contact point 218 and into the cap 240. The electricity then flows through the cap 240 and into the plurality of the bristles of the ion brush 242. The cap 240 and the plurality of bristles of the ion brush 242 may be made of any material that conducts electricity. The cap 240 may be soldered to the contact point 218, allowing electrical current to flow from the trace (214, 216), into the contact point 218, and then through the cap 240, and outward through the plurality of the bristles of the ion brush 242, dispensing ions from the plurality of bristles of the ion brush 242 to the surrounding area.

In one embodiment, the bristles of the ion brush 242 are composed of a thermoplastic polymer imbedded with conductive material that allows the polymer to conduct electricity. For example, the bristles of the ion brush 242 may be composed of polypropylene or polyethylene and impregnated with carbon. Generally, the bristles of the ion brush 242 may contain between about 20 to about 80 wt % polypropylene copolymer or polyethylene copolymer, between about 5 to about 40 wt % talc, and from about 5 to 40 wt % carbon black. However, any other resistive, inductive, reactive or conductive plastic or non-metallic material may be utilized for the bristles of the ion brush 242. The flexible ion generation device 210 may include a stiffening element within the device 210 or located at an end of one of the dielectric layer 212. The stiffening element may include an additional dielectric layer or another device that provides additional stability or stiffens the dielectric layer 212.

In another alternative embodiment, the emitter 220 may have a first end and a second end, wherein the first end of the emitter 220 is etched into the first trace 214 and/or the second trace 216 and extends to a point. The second end of the emitter 220 has a gradually reducing width that terminates at a sharp point, allowing ions to flow therefrom. The point of the emitter 220 is not connected, coupled, or engaged to the dielectric layer 212 and may extend outwards from the dielectric layer 212. In other words, the emitter 220 and/or point of the emitter 220 may extend beyond the top side or bottom side of the dielectric layer 212. The point may be coated or plated with a corrosion resistant layer such as gold or other coating material.

The point disposed on the second end of the emitter 220 allows ions to flow therefrom. It is important to note that the dielectric layer 212 does not cover the point, thus allowing ions to flow from the point and into the surrounding air. The dielectric layer 212 adjacent the point may be cut-away, pulled back, or otherwise removed, allowing ions to freely flow from the end of the point.

The emitters 220 may produce negative ions or positive ions for emission into the surrounding air. For example, the embodiment illustrated in FIG. 1, the emitters 220 engaged to the first trace 214 or the contact points 218 of the first trace 214 may emit positive ions and the emitters 220 engaged to the second trace 216 or the contact points 218 of the second trace 216 may emit negative ions. In the embodiment illustrated in FIG. 12, the emitters 220 emit either positive or negative ions.

The device 210 may be positioned and secured in place within a conduit or the housing of the air handler unit, such as a duct, such that the emitters 220 are aligned generally perpendicularly to the direction of the airflow across the device, to prevent recombination of the positively charged ions with the negatively charged ions, if the flexible ion electrode 210 produces both negative and positive ions, as opposed to unipolar ionization of negative ions or positive ions.

The device 210 may be positioned in place or engaged to an air handler unit or like device by a flexible ion generator attachment device 244 and the power supply device 230 may contain a power supply device attachment device 246. As shown in FIGS. 9, 10-12, the flexible ion generator attachment device 244 is engaged to the bottom side of the dielectric layer 212. Likewise, the power supply device attachment device 246 is engaged to the external side of the base of the power supply device 230. The flexible ion generator attachment device 244 and the power supply device attachment device 246 may be double sided tape, wherein one side of the tape is engaged to the bottom side of the dielectric layer 212 and the external side of the base of the power supply device 230. The second side of the double sided tape is engaged to the place, air handler unit, or other location where the device 210 is desired to be engaged. Alternatively, the flexible ion generator attachment device 244 and the power supply device attachment device 246 may be a hook and loop fastener, commonly sold under the trademark Velcro®, wherein the hook portion is engaged to the bottom side of the dielectric layer 212 and the external side of the base of the power supply device 230, and the loop portion is engaged to the place, air handler unit, or other location where the device 210 is desired to be engaged, for selectively securing the device 210. Alternatively, the loop portion is engaged to the bottom side of the dielectric layer 212 and the external side of the base of the power supply device 230, and the hook portion is engaged to the place, air handler unit, or other location where the device 210 is desired to be engaged, for selectively securing the device 210.

As illustrated in FIG. 13 in an alternative embodiment, the emitters 220 disposed along the first trace 214 may face opposite each other. In other words, the emitters 220 may alternate positions along the length of the first trace 214. As shown, the first emitter 220 faces towards one side, the second emitter 220' faces towards the opposite side, the third emitter 220" faces towards the same side as emitter 220, and the fourth emitter 220"" faces towards the same side as emitter 220' and so on.

As illustrated in FIG. 14, the emitters 220 may be positioned where they extend upwardly from the dielectric layer 212. The cap 240 is positioned on the contact point 218 or the trace 214 and the ion brush 242 with its plurality of bristles extends upwardly from the dielectric layer 212 and not laying on the dielectric layer 212 or in parallel with the dielectric layer 212 as shown in FIGS. 8-12.

The treatment of air by delivery of unipolar or bipolar ionization to an airflow within a conduit according to the systems and methods of the present invention may be utilized for various purposes. For example, application of bipolar ionization to an airflow within an HVAC conduit such as an air handler housing or duct may be utilized to abate allergens, pathogens, odors, gases, volatile organic compounds, bacteria, virus, mold, dander, fungus, dust mites, animal and smoke odors, and/or static electricity in a treated air space to which the airflow is directed. Ionization of air in living and working spaces may reduce building related illness and improve indoor air quality; and additionally can reduce the quantity of outside air needed to be mixed with the treated indoor air, reducing heating and cooling costs by enabling a greater degree of air recirculation.

The flexible ion generator device 210 may be used in a variable refrigerant volume (VRV) system having a shared outdoor heat exchanger and a plurality of individual air handler units. Alternatively, the HVAC system can take the form of a variable air volume (VAV), constant air volume (CAV), variable refrigerant flow (VRF) or other forms of heating, ventilation and air conditioning system.

In typical fashion, the shared outdoor heat exchanger comprises a condenser coil, compressor and fan; the individual air handler units each comprise a fan, expansion valve, heating/cooling coil(s), and a filter; and refrigerant lines connect the shared outdoor heat exchanger to the individual air handler units. Return air from the conditioned space and/or fresh air from an exterior space is treated and delivered to a conditioned air space via the individual air handler units. The outdoor heat exchanger discharges waste heat from the conditioned air space to the ambient surroundings, and/or transfers heat from a cooled zone to a heated zone. The flexible ion generator device 210 may be mounted after the filter and before the heating or cooling coil. Alternatively, the flexible ion generator device 210 may be mounted adjacent the heat exchanger located within the conduit.

Inlet airflow flows through a conduit such as the housing of the air handler unit or a duct is filtered through a filter such as a mesh, screen, paper, cloth or other filter media. A filtered airflow downstream of the filter is treated by discharge of bipolar ionization from the flexible ion generator device 210 to form an ionized airflow. The flexible ion generator device 210 comprises a stream of negatively charged (−) ions and/or a stream of positively charged (+).

The ionized airflow enters the inlet of a fan or blower for delivery to the treated air space, and is optionally heated or cooled by passing across or through a cooling coil or heating element. The coil, filter, ion generator, and fan are optionally mounted within a housing of the air handler unit.

The length and thickness of the flexible ion generator device 210 may vary according to a number of physical or electrical parameters and desires by the user. The flexible ion generator device 210 of the present invention is provided to the user with a dielectric layer 212 having at least a first trace 214 and optionally a second trace 216, with each trace (214, 216) having either a contact point 218 and emitter 220 or only an emitter 220 engaged to the trace (214, 216). The user is able to cut the dielectric layer 212 to any length they desire without disrupting the performance of the device 210. For example, if the device 210 has dielectric layers that is 5 feet in length, but the user needs a dielectric layer that is only 4 feet, the user can cut a foot off the dielectric layer without disrupting the performance of the device 210.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:

1. A flexible ion generator device, comprising:
   a dielectric layer having a first end, a second end, a first side, a second side, a top side, and a bottom side;
   at least one trace positioned on the dielectric layer and having a plurality of contact points along the trace; and
   a plurality of emitters are engaged to the contact points along the trace.

2. The flexible ion generator device according to claim 1, wherein the emitter is composed of a cap with an ion brush containing a plurality of bristles extending therefrom.

3. The flexible ion generator device according to claim 1, wherein the composition of the trace is selected from the group consisting of copper, brass, stainless steel, titanium, gold, silver, tungsten, and carbon.

4. The flexible ion generator device according to claim 1, wherein the at least one trace is substantially within a parallel plane in relation with either the first side or the second side of the dielectric layer, and periodically, the at least one trace extends downwardly from the parallel plane to a first side of the contact point, the at least one trace extends from a second side of the contact point back towards the parallel plane and extends along the parallel plane.

5. The flexible ion generator device according to claim 1, wherein the at least one trace is positioned in close proximity to the first side of the dielectric layer and generally is parallel with the first side of the dielectric layer, at predetermined distances along the length of the at least one trace, the at least one trace extends downwardly towards the second side of the dielectric layer to a first side of the contact point and then from a second side of the contact point, the at least one trace extends towards the top side of the dielectric layer and extends generally parallel with the top side of the dielectric layer.

6. The flexible ion generator device according to claim 1, further comprising a coupler having a base that extends to an outer edge and a first pair of opposed sidewalls and a second pair of opposed sidewalls extend upwardly from the outer edge to an upper edge, forming a cavity therein, a top portion is disposed on the upper edge, a slot is formed in one of the sidewalls extending from the external surface to the internal surface for receiving the first end of the dielectric layer.

7. The flexible ion generator device according to claim 1, further comprising an attachment device disposed on the bottom side of the dielectric layer.

8. A flexible ion generator device, comprising:
   a dielectric layer having a first end, a second end, a first side, a second side, a top side, and a bottom side;
   at least one trace positioned on the dielectric layer and having a plurality of
   emitters engaged to the at least one trace, wherein the trace extends along the top side of the dielectric layer along a substantially parallel plane with respect to either the first side or the second side and in predetermined locations periodically along the length of the dielectric layer, the at least one trace extends downwardly from the parallel plane for a distance and then upwardly towards the parallel plane.

9. The flexible ion generator device according to claim 8, wherein the emitter
   is composed of a cap with an ion brush containing a plurality of bristles extending therefrom.

10. The flexible ion generator device according to claim 8, wherein
    the dielectric layer may be cut anywhere along its length without affecting the operating of the device.

11. The flexible ion generator device according to claim 8, wherein at least one
    emitter extends upwardly from the dielectric layer.

12. The flexible ion generator device according to claim 8, wherein the emitters
    face toward either the first side or the second side in an alternating arrangement.

13. The flexible ion generator device according to claim 8, further comprising
    a power supply device engaged to the flexible ion generator device.

14. A flexible ion generator device, comprising:
    a dielectric layer having a first end, a second end, a first side, a second side, a top side, and a bottom side;
    a trace positioned on the dielectric layer and having a plurality of
    emitters engaged to the trace, wherein the trace extends along the top side of the dielectric layer and along a substantially parallel plane with respect to either the first side or the second side and in predetermined locations periodically along the length of the dielectric layer, the trace extends downwardly from the parallel plane for a distance and then upwardly towards the parallel plane.

15. The flexible ion generator device according to claim 14, further comprising
    a power supply device engaged to the flexible ion generator device for supplying power.

16. The flexible ion generator device according to claim 14, wherein the emitter
    is composed of a cap with an ion brush containing a plurality of bristles extending therefrom.

17. The flexible ion generator device according to claim 14, further comprising
    a plurality of contact points along the trace for receiving the plurality of emitters.

18. The flexible ion generator device according to claim 14, further
    comprising a coupler having a base that extends to an outer edge and a first pair of opposed sidewalls and a second pair of opposed sidewalls extend upwardly from the outer edge to an upper edge, forming a cavity therein, a top portion is disposed on the upper edge, a slot is formed in one of the sidewalls extending from the external surface to the internal surface for receiving the first end of the dielectric layer.

\* \* \* \* \*